United States Patent [19]
Girodo et al.

[11] Patent Number: 5,226,415
[45] Date of Patent: Jul. 13, 1993

[54] METHOD AND APPARATUS FOR CONTROLLING A DUAL-CHAMBER PACEMAKER IN RESPONSE TO PHYSIOLOGICAL AND PATHOLOGICAL ATRIAL EVENTS

[75] Inventors: Sylvie Girodo, Montrouge; Odile Malherbe, Cachan; Marcel Limousin, Montrouge, all of France

[73] Assignee: ELA Medical, Montrouge, France

[21] Appl. No.: 796,061

[22] Filed: Nov. 22, 1991

[30] Foreign Application Priority Data

Nov. 30, 1990 [FR] France ................... 90 15011

[51] Int. Cl.⁵ ............................. A61N 1/365
[52] U.S. Cl. .............................. 128/419 PG
[58] Field of Search ................... 128/419 PG

[56] References Cited

U.S. PATENT DOCUMENTS

| | | | |
|---|---|---|---|
| 4,343,311 | 8/1982 | Markowitz | 128/419 PG |
| 4,344,437 | 8/1982 | Markowitz | 128/419 PG |
| 4,378,020 | 3/1983 | Nappholz et al. | 128/419 PG |
| 4,412,541 | 11/1983 | Schaldach et al. | 128/419 PG |
| 4,429,697 | 2/1984 | Nappholz et al. | 128/419 PG |
| 4,432,362 | 2/1984 | Leckrone et al. | 128/419 PG |
| 4,467,810 | 8/1984 | Vollman | 128/419 |
| 4,515,161 | 5/1985 | Wittkampf et al. | 128/419 |
| 4,554,920 | 11/1985 | Baker, Jr. et al. | 128/419 PG |
| 4,554,921 | 11/1985 | Boute et al. | 128/419 PG |
| 4,712,556 | 12/1987 | Baker et al. | 128/419 PG |
| 4,714,079 | 12/1987 | Hedberg et al. | 128/419 PG |
| 4,781,194 | 11/1988 | Elmqvist | 128/419 PG |
| 4,788,980 | 12/1988 | Mann et al. | 128/419 PG |
| 4,890,617 | 1/1990 | Markowitz et al. | 128/419 |
| 4,932,406 | 6/1990 | Berkovits | 128/419 PG |
| 4,944,298 | 7/1990 | Sholder | 128/419 PG |
| 4,967,746 | 11/1990 | Vandegriff | 128/419 PG |

FOREIGN PATENT DOCUMENTS

318304 5/1989 European Pat. Off. .

Primary Examiner—William E. Kamm
Attorney, Agent, or Firm—Davis Hoxie Faithfull & Hapgood

[57] ABSTRACT

A method for controlling the cardiac rhythm of a wearer of a dual-chamber pacemaker. A post-atrial atrial refractory period (PAARP) is defined. Any depolarization of the atrium that occurs during the PAARP is defined as pathological. An atrial-ventricular delay is not triggered in response to a pathological depolarization.

33 Claims, 2 Drawing Sheets

Microfiche Appendix Included
(1 Microfiche, 66 Pages)

METHOD AND APPARATUS FOR CONTROLLING A DUAL-CHAMBER PACEMAKER IN RESPONSE TO PHYSIOLOGICAL AND PATHOLOGICAL ATRIAL EVENTS

This specification is accompanied by a microfiche appendix including one film and 66 pages.

A portion of the disclosure of this patent document contains material which is subject to copyright protection. The copyright owner has no objection to the facsimile reproduction by any one of the patent disclosure, as it appears in the Patent and Trademark Office patent files or records, but otherwise reserves all copyright rights whatsoever.

FIELD OF THE INVENTION

This invention relates to a method for controlling the cardiac rhythm of a patient wearing a dual-chamber pacemaker, more particularly to avoiding an exaggerated increase of the cardiac rhythm in response to an isolated atrial extrasystole and/or in the case of an established atrial tachycardia.

BACKGROUND OF THE INVENTION

In a known manner, there are memorized in the known pacemakers intended for controlling the heart, two values of frequencies for the stimulation of the ventricle. One value is the basic frequency or the minimum frequency of stimulation, and the other value is the maximum frequency beyond which it is hazardous to stimulate the ventricle. When the pacemaker detects an increase in atrial activity, it stimulates the ventricle at a frequency approaching the atrium frequency, however, without exceeding the maximum set frequency.

The first problem which arises in known cardiac pacemakers is the difficulty in distinguishing a physiological acceleration of the atrial rhythm from a pathological acceleration.

A second problem which arises in presence of an acceleration of the atrium beyond the maximum frequency is to appreciate the duration during which the heart is stimulated at a fast frequency, before switching to slow-down or fall back mode towards a basic frequency.

The third problem during this slowing-down procedure is the dissociation between depolarization at the atrial stage and depolarization at the ventricular stage.

In existing pacemakers, these problems are solved in an imperfect manner. U.S. Pat. No. 4,467,810, for instance describes a pacemaker in which the stimulation procedure in the known 2/1 mode (a ratio of two atrial depolarizations to one ventricular depolarization) takes place as soon as the depolarization frequency of the atrium reaches the reference frequency, and depolarizations of the atrium which occur at a frequency exceeding a programmed reference frequency are systematically ignored. Besides this, the described pacemaker uses a fall-back procedure, that is, a procedure for slowing down the rhythm of stimulation of the ventricle, independently of the atrium rhythm.

There is, however, a continuing need for improved pacemaker devices and methods of cardiac activity signal processing for controlling cardiac rhythm particularly in the presence of atrial extrasystoles.

SUMMARY OF THE INVENTION

It is, therefore, an object of the present invention to control the cardiac rhythm in a manner that avoids the aforementioned drawbacks.

It is another object of the invention to control the cardiac rhythm in response to the sensed acceleration of atrial events.

It is another object to improve the determination of whether atrial acceleration is physiological or pathological.

It is another object of the invention to minimize the acceleration of ventricular stimulation in response to the pathological acceleration of atrial activity.

Accordingly, the present invention provides for monitoring atrial depolarization, identifying sensed atrial acceleration as physiological or pathological, dissociating the atrium and the ventricle when a pathological (abnormal) acceleration of the atrium is detected by slowing-down the ventricular rhythm, and maintaining an atrial-ventricular association in the other cases, within the limit of the maximum frequency of ventricular stimulation.

One embodiment of the invention provides a method for controlling the cardiac rhythm of a wearer of a dual-chamber pacemaker, characterized by defining a post-atrial refractory period (hereinafter designated as "PAARP"), sensing the depolarization of the atrium as a "P" wave, defining any depolarization of the atrium during the PAARP as pathological, and not triggering, upon the detection thereof, the atrial-ventricular delay so as not to stimulate the ventricle.

Preferably, the PAARP is selected to be a percentage of or a fraction that is between 0.7 and 0.8 times, more preferably 0.75 times, the time interval between the two previous physiological "P" waves. In the case of the presence of an atrial or ventricular extrasystole, as sensed by the pacemaker, the PAARP is instead defined as a fraction of the sliding average taken during the eight most recent physiological atrial events. In other words, if the latest occurring "P" wave corresponds to an atrial or a ventricular extrasystole, the PAARP is based on a fraction of the average of a selected number, preferably 8, preceding P-P intervals, and otherwise the PAARP used is equal to a fraction of the last acquired PP interval e.g., 0.7 to 0.8, preferably 0.75.

The PAARP is, however, provided with a maximum duration selected from between 400 and 600 ms, more preferably 560 ms. One reason the limit is applied to provide for sensing rapid atrial events beyond, e.g., 120 beats per minute.

The detection of a "P" wave occurring during the PAARP triggers an atrial escape interval having a duration that is set equal to the PAARP. In the absence of a detection of a subsequent "P" wave, one stimulates the atrium at the end of the longest delay as between either (1) last set PAARP or (2) the atrial escape interval triggered at the time of the previous "P" wave.

In the case of detection of a "P" wave after the expiration of the PAARP, or in case of stimulation of the atrium, whichever occurs, one triggers an atrial-ventricular delay of a minimum set duration. At the end of the minimum atrial-ventricular delay, the ventricle is stimulated if the elapsed time since the last ventricular stimulation is longer than the Pmin period, corresponding to the maximum selected frequency of stimulation. If, however, at the end of the minimum atrial-ventricular delay the delay needs to be extended to prevent exceeding the maximum frequency of stimulation, the delay will be extended and one will then trigger, after the stimulation of the ventricle, a PAARP, the duration of which is set to equal the time which separates two stimulations at the maximum frequency, reduced by the value of the minimum atrial-ventricular delay. The Pmin period is set for the patient's condition and characteristics.

After having observed the establishing of the tachycardia during a defined time, preferably to 30 seconds, one triggers the slow-down or fall-back mode of the pacemaker which provides arbitrarily lowering the ventricular stimulation frequency, down to a stable frequency set, for example, at 70 beats/minute.

However, when operating in the fall-back mode, in accordance with the invention, the delay between "P" waves is monitored. When the minimum interval between two consecutive "P" waves over a preselected number of cycles, e.g., eight, becomes larger than the Pmin period, the fall-back mode is exited and operation reverts to the initial mode of heart stimulation where the ventricle and atrium are associated.

Another aspect of the invention is directed to apparatus for controlling a dual-chamber pacemaker having a sensor for monitoring atrial and ventricular depolarization, electrodes for stimulating the atrial and ventricle, and a fall-back mode for reducing the rate of ventricular stimulation from a maximum rate to a base rate, characterized by:

a circuit for detecting P waves corresponding to atrial depolarization events;

a circuit for initiating a post-atrial atrial refractory period following an atrial depolarization;

a circuit for determining that a P wave that occurs during an initiated PAARP is pathological and a P wave that occurs after the initiated PAARP is physiological;

a circuit initiating a selected atrial-ventricular delay in response to a P wave occurring after the initiated PAARP and for not initiating any atrial ventricular delay in response to a P wave occurring during the initiated PAARP.

Preferably, the PAARP is selected to be the multiple of a fraction selected from between 0.7 and 0.8 times the time interval between two previous physiological P waves, and, in response to the occurrence of a pathological atrial or ventricular depolarization, the PAARP is selected by the multiple of a fraction selected from between 0.7 and 0.8 times the average of the eight preceding physiological P wave intervals.

The apparatus may further comprise a circuit for triggering an atrial escape interval having a duration equal to the selected PAARP upon the detection of a P wave occurring during the initiated PAARP, wherein the atrium is stimulated at the end of the longest delay as between (1) the PAARP interval and (2) the atrial escape interval triggered at the time of the previous "P" wave in the absence of a detection of a subsequent "P" wave.

The apparatus is preferably constructed in the form of a microprocessor device, e.g., an eight bit microprocessor, having a suitable memory device, e.g., RAM and ROM, analog to digital and digital to analog converters, data bus, protection circuits, and software instructions to sense signals corresponding to atrial and ventricular events, initiate time delays and assess the occurrence of events relative to time delays, and to provide output signals for causing atrial and ventricular stimulation, i.e., for implementing the method steps and functions described herein.

BRIEF DESCRIPTION OF THE DRAWINGS

Further characteristics of this invention will emerge from the following description made with reference to the appended drawings, in which like reference characters refer to like elements and in which.

DETAILED DESCRIPTION OF THE INVENTION

Figure 1:
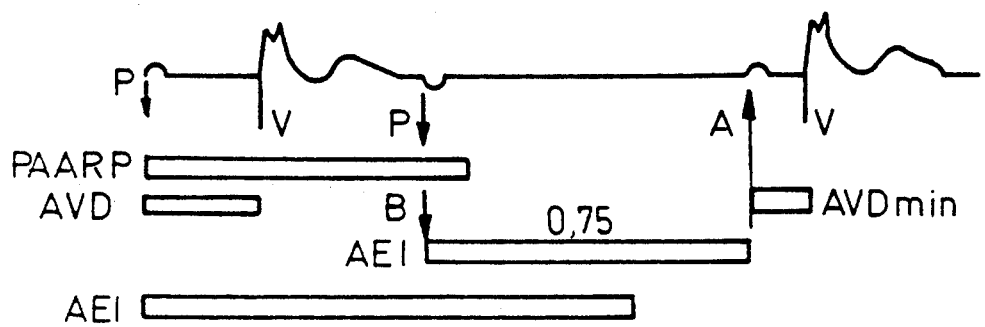
FIG. 1 is a diagram illustrating an embodiment of the invention for controlling the cardiac rhythm in an example of an isolated atrial extrasystole.
Figure 2:
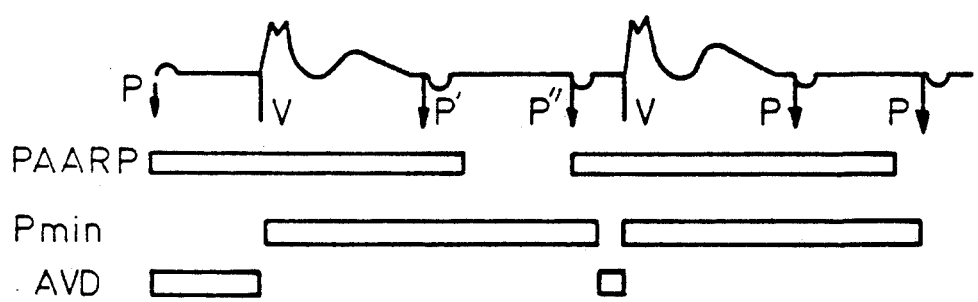
FIG. 2 is a diagram illustrating an embodiment of the invention in an example of atrial tachycardia of a frequency less than twice the maximal frequency of stimulation.
Figure 3:
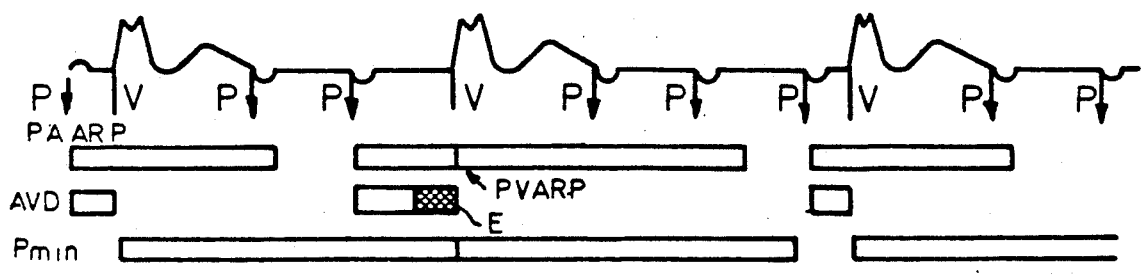
FIG. 3 is a diagram illustrating an embodiment of the invention in an example of atrial tachycardia having a frequency which is more than twice the maximal frequency of stimulation.

Referring to FIGS. 1-3, a preferred embodiment of the method of the present method is illustrated in different operating circumstances. One aspect of the invention is a method for controlling the heart rhythm that distinguishes itself from the prior known methods by detecting an acceleration of the activity of the atrium for use as a new physiological parameter, and ascertaining whether an acceleration is a pathological acceleration. For this purpose, the atrial and ventricular absolute refractory periods that are triggered after each depolarization of the ventricle are modified. During these periods one does not monitor what is taking place in the atrium and one does not want to stimulate the ventricle. These periods, which are usually equal in prior devices, are, according to the invention, reduced, preferably to their minimum necessary duration. The ventricular absolute refractory period varies little from the usual values, in the order of 204 to 350 ms, more preferably reduced to about 204 ms. The atrial absolute refractory period is limited to the recovery time required for the signal sensing and processing amplifiers of the pacemaker, which is approximately 110 ms. In this manner, it is possible to examine and to take into account what is occurring at the atrium level, much more rapidly and during 94 to 240 additional milliseconds at each cycle. The atrial absolute refractory period is thus reduced to a value such that one can more precisely observe an acceleration of the atrial rhythm and determine whether this acceleration is pathological or physiological.

The method according to this invention for controlling the cardiac rhythm includes defining a period during which any depolarization of the atrium is determined to be pathological. This period, designated as the post-atrial refractory period (PAARP) is selected to have a duration from selected 0.7 and 0.8 times the time separating two "P" waves; provided, however, that the duration is maintained less than a value selected from between 400 and 600 ms. These values are selected to minimize the likelihood of taking into account physiological accelerations, which do not exceed these values in a sustained manner. In other words, only the pathological accelerations give variations large enough for exceeding these values. Preferably, the PAARP is equal to 0.75 times the time separating two "P" waves, and is maintained below 560 ms. Preferably, the maximum PAARP interval may be programmed and otherwise a default or a preselected interval, e.g., 560 ms, is used. This provides for initiating operation of the method and apparatus until sufficient data can be obtained.

The duration separating two "P" waves is measured between two "P" waves designated as "competent", that is, between depolarizations of the atrium which have triggered an atrial-ventricular delay (AVD).

As indicated above, when the previous cycle was physiological (normal) the delay between two "P" waves which is used when a depolarization of the atrium is detected is the actually measured delay, and when the previous cycle was pathological, the delay used is the average of the measured delay values during the last eight normal cycles.

Thus, in accordance with the invention, during the PAARP which is triggered by a depolarization of the atrium, one observes whether or not a P wave occurs. Depolarization "P" waves are represented by the downward arrows P in the drawings. If the first next "P" wave occurs after the end of the PAARP, then it is considered that the atrium has not undergone an acceleration greater than 25%, and one triggers in the usual manner an atrial-ventricular delay (AVD).

Referring now to FIG. 1, if a following "P" wave is detected during the PAARP, it is concluded that such a following P wave corresponds to an atrial extrasystole and an abnormal cardiac cycle and one does not trigger an atrial-ventricular delay. Upon the detection of this following "P" wave during the PAARP, one triggers (represented by the downward arrow B) an atrial escape interval (AEI) having a duration selected to be equal to the PAARP. The atrial escape interval is, in a manner known per se, the time at the end of which the atrium must be stimulated, unless a spontaneous depolarization has occurred.

At the end of the longest delay interval, that is, either at the end of the atrial escape interval AEI following the following "P" wave detected during the PAARP triggered by the first "P" wave (see the upwardly pointing arrow A), or else at the end of the atrial escape interval triggered by the first "P" wave, one stimulates the atrium and triggers an atrial-ventricular delay AVD equalling the programmed minimum atrial-ventricular delay. The minimum atrial-ventricular delay is selected in order not to lengthen the ventricular cycle too much, and may be adjusted.

At the end of the atrial-ventricular delay, the ventricle will be stimulated (represented by the vertical line V), provided that the Pmin period elapsed since the last stimulation of the ventricle.

Referring to FIG. 2, the atrial tachycardia illustrated has a frequency that is less than twice the maximal frequency of stimulation. The occurrence of the P wave P' before the end of the PAARP interval does not trigger an atrial-ventricular delay period. The next sensed P wave P, which occurs after the PAARP, will trigger the minimum AVD and at the end of the AVD the ventricle is stimulated. To respect the synchronization, the minimum AVD period is used. That P wave P" also triggers a new atrial escape interval which, in turn, will yield a ventricle depolarization at the conclusion of the next atrial-ventricular delay (not shown in FIG. 2). Thus, the ventricle will then be stimulated only once, while the atrium will have depolarized itself twice. This provides for an association between the atrium and the ventricle known as 2/1, to minimize, if not eliminate, acceleration of the ventricle.

Referring to FIG. 3, the atrial tachycardia illustrated has a frequency of more than twice the maximum stimulation frequency. The first "P" wave sensed outside of the previously triggered PAARP triggers a PAARP and an AVD such that the AVD ends before the end of the previously triggered Pmin interval. Accordingly, the AVD is lengthened by an amount that coincides with the end of the Pmin period (represented by the cross-hatched area E). At the end of this Pmin period, the ventricle is stimulated and one replaces the PAARP triggered by the "P" wave with a post-ventricular atrial refractory period ("PVARP"), the duration of which equals the minimum period Pmin less the minimum AVD:

$$PVARP = Pmin - AVD\ min = Pmin - 31ms.$$

The first "P" wave detected after the PVARP triggers a minimum AVD of 31 ms.

If the tachycardia is established, one has then an atriumventricle association of 3/1 for which there is one stimulation of the ventricle for three detections of the atrium. This 3/1 cycle will alternate with 2/1 cycles in a known matter.

The utilization of this principle of the PAARP and of its operating mode makes it possible to shift the ventricular rhythm to the (2/1, 3/1) mode, or eventually to the (n/1, (n+1)/1) mode in case of disturbances of the atrial rhythm, and thus to avoid a useless increase of the ventricular stimulation frequency.

Should any of the above-described situations perpetuate itself, it will then be found that one is in presence of a pathological tachycardia. At the end of a selected delay, which may, for example, be set at 30 seconds, one triggers the fallback mode of the operation of the pacemaker during which the ventricle is dissociated from the atrium, and the ventricle stimulation frequency is arbitrarily and gradually lowered down to a stable frequency set, for example, at 70 beats per minute. The fall-back mode, which does not form a part of this invention, has been previously described in the literature see, e.g., U.S. Pat. No. 4,467,810. The ventricle stimulation slow-down is preferably made in accordance with the pacemaker mode usually designated as VVI which means that the detection of a depolarization of the ventricle inhibits the stimulation which it should have received.

During operation in the fall-back mode, the interval between two consecutive "P" waves is monitored. When the PP interval over 8 cycles becomes longer than the minimum Pmin period corresponding to the maximum stimulation frequency programmed for the ventricle, one exits from the fall-back mode and reverts to the initial mode of heart stimulation.

Establishing the 30 seconds delay before triggering the fall-back mode makes it possible to trigger fall-back only in the case of sustained tachycardia. Of course, a delay other than 30 seconds could be used to indicate the sustained tachycardia and a number of cardiac cycles other than 8 could be used.

Advantageously, the present invention minimizes the likelihood of generating, if not eliminating entirely, a fast ventricular rhythm during a tachycardia, irrespective of its duration.

The method of the invention is preferably performed by a computer, more preferably, a microprocessor device having software instructions in an associated memory device and sensors suitable for performing the measurements described and providing stimulating pulses as appropriate, including without limitation, a microprocessor controlled dual chamber pacemaker having input parameters programmable for the patient's characteristics in the known manner. Appropriate devices for converting analog circuit signals to digital signals and vice versa may be provided. It is to be understood, however, that the method also may be performed by suitable analog circuit devices, and by a combination of digital and analog circuits. All of the foregoing components are conventional.

Figure 4:
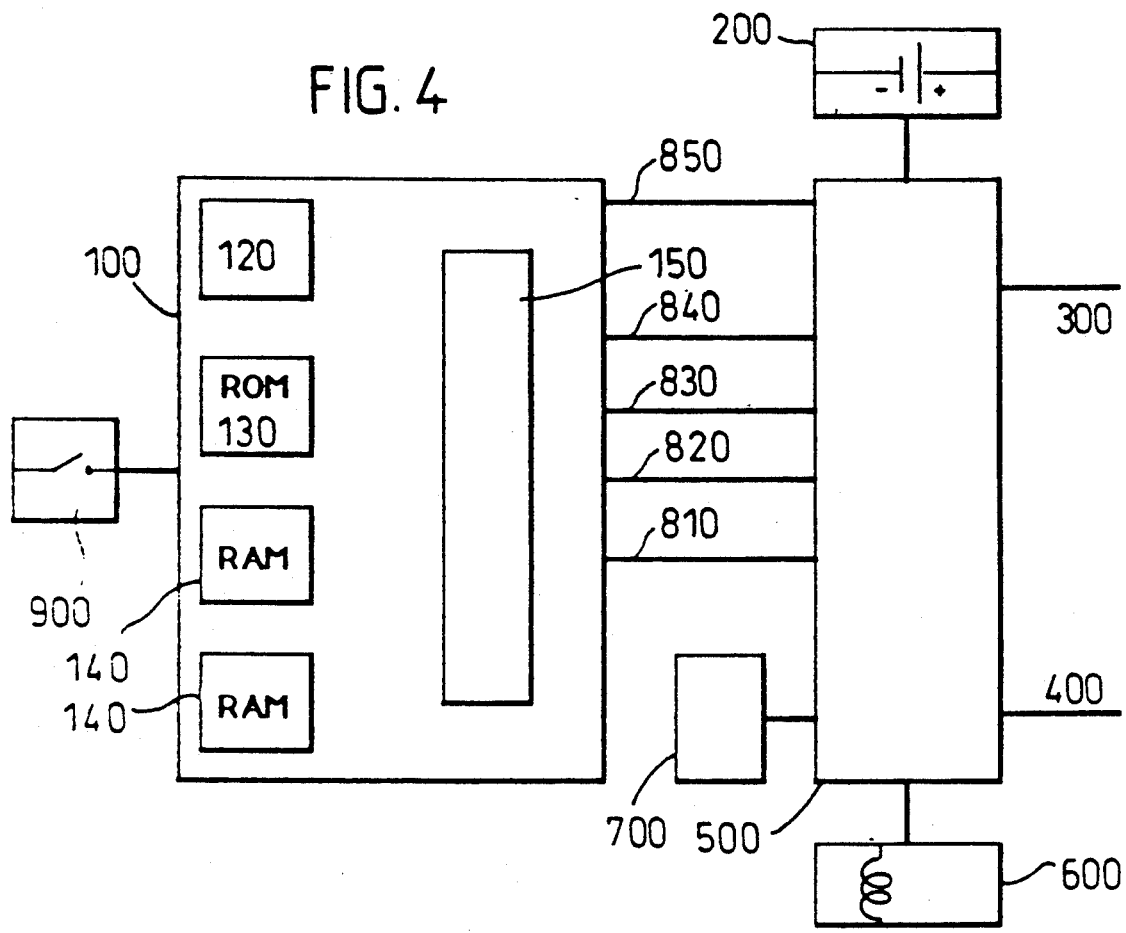
FIG. 4 is a schematic block diagram of an apparatus in accordance with the present invention.

Referring to FIG. 4, a schematic embodiment of a dual chambered pacemaker in accordance with the present invention is illustrated. The apparatus includes a microprocessor 100, a battery 200, an atrial sensing and stimulating catheter 300, a ventricular sensing and stimulating catheter 400, an analog signal acquisition and conversion circuit 500, a telemetry antenna 600 and an associated reed switch 900, a clock oscillator 700 and appropriate data and control buses.

Microprocessor 100 is preferably an eight bit device including a central processing unit 120, a ROM-type memory device 130 which includes software instructions for operating the pacemaker including inter alia in accordance with the present invention, one or more RAM-type memory devices 140 for data storage, manipulation and other memory related functions, and an input/output interface 150 for communicating within microprocessor 100 and between microprocessor 100 and other components of the pacemaker. Input/output interface 150 includes, for example, a data bus 810 for data transmission, an address bus 820, a control bus 830, all of which are conventional and dependent on the microprocessor device used.

Catheters 300 and 400 are conventional pacemaker catheter electrodes and preferably have associated conventional protection circuits (not shown) to protect the pacemaker and patients from external signals in the usual manner.

Circuit 500 provides for converting analog cardiac atrial and ventricular signals to digital signals (and for converting digital signals to analog signals) for signal processing by microprocessor 100, and does not itself form any part of the present invention.

Antenna 600 is used for remote programming of microprocessor 100 in cooperation with actuation reed switch 900, in the conventional manner. Antenna 600 also may be provided with suitable protection circuits. Oscillator 700 provides the base clock frequency for operating the data acquisition and processing functions. The foregoing components are available in one form or another and may be assembled by a person of ordinary skill in the art.

A preferred microprocessor controlled dual chamber pacemaker for use with the present invention is an atrial based pacemaker such as CHORUS II ™, implantable dual chamber pulse generator DDD MO, available from Ela Medical, Montrouge, France. The model CHORUS II 6200 Series, specifically the 6234, includes an operating mode that uses the present invention when the "fallback" algorithm is programmed on.

Figure 5:
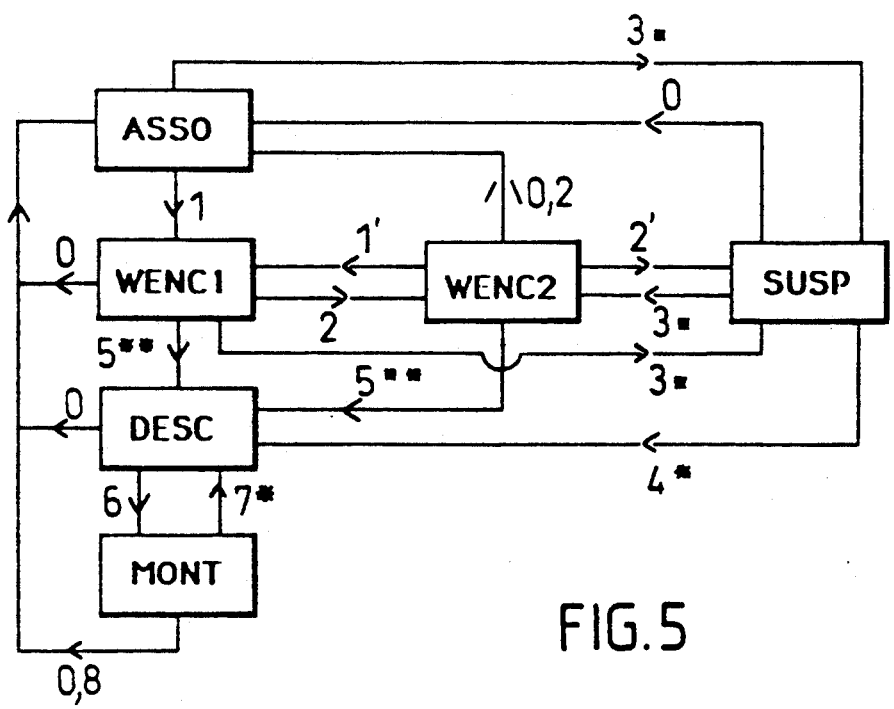
FIG. 5 is a state diagram of the operation of a preferred embodiment of the present invention.

Referring to FIG. 5, the following Tables I and II, and the software, the state diagram of the operation of a preferred embodiment of the invention is described.

The software contains program instructions and parameters in addition to those that pertain to the present invention, which place the use of the invention in context.

The state diagram contains the following states: ASSO, WENCI, WENC2, SUSP, DESC, and MONT. ASSO is the variable state in which the atrium and ventricle are controlled in association in response to the occurrence of P waves determined to be physiological. The occurrence of a P wave during the PAARP triggered by a previous P wave is determined to be pathological and places the device in state SUSP, which is a suspicion state, in which for the following sensed P wave, the ventricular pacing rate is limited to a rate of, e.g., 120 beats/min, with the corresponding Pmin interval, and a minimum atrial-ventricular delay of, e.g., 31 msec, is started. If there has not been a sustained atrial tachycardia for the predetermined time of 30 seconds, then the device will change to state WENCI or WENC2 in which the pacemaker operates in a Wenckebach mode. In the WENCI Wenckebach mode, the PR interval is delayed and there is a 2:1 association. If the next cycle has a long PP interval and a long VV interval then the device may decide to leave WENCl. If the next PP interval is shorter, then the device goes to WENC2, where it will not restore the function of the device in the 1:1 association. If the next PP interval is not shorter, then the device will leave the Wenckebach mode (after two long cycles) and return to ASSO.

If in the SUSP state and the tachycardia duration exceeds the predetermined time limit, then the device changes to state DESC, in which the pacemaker reverts to its fallback mode of pacing. The fallback mode preferably places the pacemaker in the VDI operating mode with continued sensing of P waves. In this mode, the ventricular escape interval is lengthened by a preset time, e.g., 31 msec, every eighth cycle until the ventricle pacing rate is reduced to the preset rate limit of, e.g., 70 beats/min where it is maintained for as long as the sensed atrial rate is higher than the lower of the maximum ventricular stimulation rate and programmed a rate of, e.g., 120 beats/min. When the sensed atrial rate falls below one of the thresholds, the device enters the state MONT, in which the pacemaker exits the fallback mode of operation and increases the ventricular pacing to correspond to the atrial detection or stimulation. In this state, the ventricular pacing interval is incremented by a preset amount, e.g., 63 msec, every eight cardiac cycles until it reaches the sensed atrial rate. At that point, there is resynchronization of the atrium ventricle and the device returns to the ASSO state.

It is noted the atrial rate may increase gradually to a maximum rate without entering state SUSP. Therefore, each Wenckebach state is provided with a counter and a maximum number of Wenckenbach cycles, e.g., 2000, after which the device will directly change to state DESC.

In the following description, the use of quotation marks indicates a software variable that is a preset or programmable value, a calculated value based on sensed measurements or a software counter or flag, and the use of uppercase letters indicates measured parameters of cardiac activity. Also, the use of the back to back less than greater than symbols < > before a parameter X refers to not X. The variable state is "asso mode" If "flag add" is set to DDD BEHAVIOR, DDD mode, or VDD mode, the state machine determines the mode of the atrial ventricular association as a function of the atrial rhythm (P wave).

The following variables and parameters are used: "global mode" is a programmable term for configuring the pacemaker, and, for the present invention, is set to be NORM; "min per" and MINPER are the minimum period corresponding to the maximum ventricular pacing frequency; PACED V is the last ventricle stimulation event; "Flag P in prapa" is the flag that is set when a following P wave occurs before the end of the PAARP interval triggered by the preceding P wave; INT A is the time measured since the last atrial depolarization, INT V is the time measured since the last ventricular depolarization; SENSED R is the last spontaneous ventricular depolarization event, NO ESV is the presence of an atrial event in the ventricular cycle, "last PP" is the last determined PP interval based on physiological P waves, "shortest PP" is the shortest measured PP interval among the last 8 cardiac cycles, "esc int" is the atrial escape interval that is responsive to the PP intervals; "xprg fallback delay" is the externally programmed fallback delay which will cause the pacemaker to revert to the DESC mode after expiration of that delay; and GCI refers to global cycle index which maintains a count of cardiac cycles.

The conditions representing the transitions between states are set forth in Table 1.

TABLE 1

| No. | Description |
|---|---|
| 0 | "global mode" <> NORM, "flag ddd" = NO ALGORITHM, or "flag ddd" = AAA |
| 1 | INT A < "min per" and PACED V, and "flag P in prapa" = 0 |
| 1' | "flag P in prapa" = 0 and (INT A <= MINPER or (INT V <= MINPER and PACED V) |
| 2 | (INTA A > "min per" and INT V > "min per" and PACED V and "flag P in prapa" = 0) or (SENSED R and "flag P in prapa" = 0 and INT A > "min per") |
| 3 | "flag P in prapa" <> 0 (PP = 0.75* "last PP") |
| 4 | fallback delay is 30 sec |
| 5 | fallback delay is ("xprg fallback delay") |
| 6 | "shortest PP" >= "min per" and GCI = 7 |
| 7 | "shortest PP" <= "min per" and GCI = 7 |
| 8 | "esc int" is <= "shortest PP" + 31 msec and GCI = 7. |

As depicted in FIG. 5, the transition condition having the highest priority is followed by the greatest number of asterisks, except that the condition 0 has priority overall other conditions.

The table of functions and transitions is set forth in Table II below. The Old State category identifies the existing state, and provides separate transitions to New States, if any, and programming functions depending on whether the ventricle is spontaneously depolarizing, "R" and "Sensed R", or being paced, "V" and "Paced V" The additional terms referred to in Table II are: "R asynch" which indicates that the spontaneous ventricular depolarization is asynchronous, "Sensed R" which is a ventricular detection, "N" which is a flag of the consecutive cardiac cycles reflecting a pathological acceleration, which is reset to zero upon determination of physiological P wave; "avd ends" refers to the end of the atrial-ventricular delay; "Delay susp" refers to the time during which the tachycardia must continue before the state changes to DESC "nbr cycle max" refers to the maximum number of Wenckenbach cycles before reverting to state DESC "SHPP" is the shortest PP interval, "ESC INT" is the existing atrial escape interval.

TABLE II

| OLD STATE | INPUT | (IF) NEW STATE | FUNCTIONS ABCDEF HIeJKLMQRSTUVWgXYZabcdfh |
|---|---|---|---|
| ASSO | R asynch | | |
| R | Sensed R, N=0 | SUSP | |
| | Sensed R, N<>0 | SUSP | C e K V Y |
| V | Paced V, N<>0 | | |
| | (avd ends >31 ms) | SUSP | C eJ V Y |
| | (avd ends =31 ms) | SUSP | C e V Y |
| | Paced V, N=0 | | |
| | (INT A) >=MINPER | | |
| | (INT A) <MINPER | WENC1 | C I V Y |
| WENC1 | NBR cycle max | DESC | F U abc |
| V | Paced V, N=0 | | |
| | (INT v>MINPER) | WENC2 | Z |
| | ELSE | | Z |
| | Paced V, N><0 | | |
| | (avd ends >31 ms) | SUSP | E eJ |
| | (avd ends =31 ms) | SUSP | E e |
| R | Sensed R, N=0 | | |
| | INT A > MINPER | WENC2 | Z |
| | INT A <=MINPER | | |
| | Sensed R, N<>0 | SUSP | E e K |
| SUSP | Delay susp <=0 | DESC | A LM TU b |
| V | Paced V, N=0 | WENC2 | |
| | Paced V, N<>0 | | |
| | (avd ends >31 ms) | | E J |
| | (avd ends =31 ms) | | E |
| R | N=0 ESV ** | WENC2 | E h |
| | ELSE | | |
| | N<>0 | | E K |
| WENC2 | nbr cycle max | DESC | F U abc |
| V | Paced V, N=0 | | |
| | (INT V>MINPER & INT A>MINPER) | ASSO | L W f |
| | ELSE | WENC1 | I Z f |

TABLE II-continued

| OLD STATE | INPUT | (IF) NEW STATE | FUNCTIONS ABCDEF HIeJKLMQRSTUVWgXYZabcdfh |
|---|---|---|---|
| | Paced V, N<>0 | | |
| | (avd ends >31) | SUSP | E eJ |
| | (avd ends =31) | SUSP | E e |
| R | Sensed R, N=0 | | |
| | INT A >MINPER | ASSO | L W f |
| | INT A <=MINPER | WENC1 | I Z f |
| | Sensed R, N<>0 | SUSP | E e K |
| DESC | GCI=7&SHPP<MINPER | | H R TU |
| | GCI=7&SHPP>=MINPER | MONT | Q TU |
| | ELSE | | |
| MONT | GCI=7&SHPP<MINPER | DESC | S TU |
| V | GCI=7&ESCINT<= | ASSO | B C D U W X df |
| or | SHPP+31 ms | | |
| R | GCI=7 & ELSE | | Q TU |
| | ELSE | | |
| ALL* | GLOBAL MODE<>NORM | ASSO | B gX df |
| *** | FLAG DDD=NO ALGO. | ASSO | B g df |
| *** | FLAG DDD=AAI BEH. | ASSO | B g df |
| *** | PROG repli2=OFF | ASSO | B g df |

*Performed in the RESET OPTIONS of the Global Mode
**ESV is the absence of atrial events in the ventricle cycle: "H time sine last P or A" > "time between last cycle starts" + "time now"
***These three lines are performed in the updating of the telemeter
The function keys for Table II is as follows:
A - INCREMENT "stat for fallback 2"
B - ATR STATE = PRG ATR STATE
C - LOAD "delay in suspicion"
D - WRITE "stat for max time in mont or desc" & "av delay now" ="prg basic av delay"
E - DECREMENT "delay in suspicion"
F - INCREMENT "stat for 8 cycles in wenckebach" IN ANY CASE
H - WRITE "stat for shortest PP in descent"
I - SET "esc int" = "prg bas per"
J - SET "prapa time" / PV
K - SET "prapa time" / PR
L - INCREMENT "stat for 8 cycles in wenckebach" IF
M - "esc int" = "sum 8 VV"/8 + "time now"
Q - ESC INT = ESC INT − 63 ms
R - ESC INT = ESC INT − 31 ms
S - ESC INT = ESC INT − 125 ms
T - LIMIT ESC INT
U - "shortest PP" = 250 * 16 ms
V - UPDATE "table VV"
W - UPDATE "table PP"
X - UPDATE "last PP"
Y - LOAD NBR CYCLE MAX IN WENCKEBACH
Z - COUNT A CYCLE IN WENCKEBACH
a - "esc int" = "min per" + "time now"
b - LOAD "AV delay now" & RESET "prapa time"
c - INCREMENT "stat for fallback 1"
d - RESET "ven event in mont or desc counter"
e - SET "min per" = "xprg min per in repli2"
f - "min per" = "prg min per"
g - UPDATE ALL "table PP" CASE "flag atr cycle"
h - SET "flag no asso"

A preferred embodiment of a software program useful for controlling a microprocessor controlled dual-chambered pacemaker in accordance with the present invention is set forth in the microfiche appendix.

Preparation of alternate suitable software for controlling such microprocessor controlled pacemakers, and for reprogramming known micro-processor controlled dual chamber pacemakers, to operate in accordance with the present invention is believed to be well within the ability of a person of ordinary skill in the art.

One skilled in the art will appreciate that the present invention can be practiced by other than the described embodiments which are presented for purposes of illustration and not of limitation.

We claim:

1. A method for controlling a dual-chamber pacemaker having a first heart stimulation mode of operation, characterized by:
    monitoring atrial depolarization events as P waves and monitoring ventricular depolarization events, including stimulated and spontaneous events;
    selecting a post-atrial atrial refractory period (PAARP) following a P wave during which a sensed P wave is determined to correspond to a pathological atrial depolarization and after which a sensed P wave is determined to correspond to a physiological atrial depolarization;
    initiating an atrial-ventricular delay in response to a sensed P wave and stimulating the ventricle at the end of the atrial-ventricular delay if a spontaneous ventricular event is not sensed before the end of said delay; and
    blocking the initiation of the atrial-ventricular delay in response to a sensed P wave occurring during the selected PAARP.

2. A method according to claim 1, characterized in that selecting the PAARP is characterized by selecting a fraction from between 0.7 and 0.8, determining the time interval between two previous physiological P waves, and multiplying the selected fraction by the determined time interval.

3. The method of claim 2 characterized in that the fraction is 0.75.

4. A method according to claim 1, further characterized by identifying pathological ventricle depolarizations, characterized in that selecting the PAARP is characterized by selecting a fraction selected from between 0.7 and 0.8, determining the time interval between physiological P waves, determining an average of the eight preceding physiological P wave intervals, and multiplying the selected fraction by the determined average time interval in response to the occurrence of a pathological atrial or ventricular depolarization.

5. The method of claim 4 characterized in that the fraction is 0.75.

6. A method according to claim 1 characterized in that selecting the PAARP is characterized by limiting the PAARP to a duration between 400 and 600 ms.

7. The method of claim 6 characterized in that the maximum duration is 560 msec.

8. A method according to claim 1, further characterized by:
triggering an atrial escape interval having a duration equal to the PAARP upon the detection of a P wave occurring during the PAARP;
determining the longest delay as between the PAARP interval and the atrial escape interval triggered at the time of the previous P wave in the absence of a detection of a subsequent P wave; and
stimulating the atrium at the end of the longest delay.

9. A method according to claim 8, further characterized by providing an atrial-ventricular delay with a minimum duration and triggering an atrial-ventricular delay of minimum duration in response to one of a spontaneous P wave sensed outside of the PAARP and a stimulated P wave.

10. A method according to claim 9, further characterized by determining the elapsed time since the last ventricular stimulation, providing a period corresponding to a selected maximum frequency of stimulation, and stimulating the ventricle at the end of the minimum atrial-ventricular delay in response to the determined elapsed time being greater than the provided period.

11. A method according to claim 10 further characterized by providing the pacemaker with a fallback mode of operation for lowering the ventricular stimulation frequency to a stable frequency, further characterized by providing a defined time, determining the occurrence of pathological P waves as a tachycardia, and operating the pacemaker in the fallback mode in response to the tachycardia occurring beyond the defined time.

12. A method according to claim 11 in which operating in the fallback mode is further characterized by monitoring the interval between two consecutive P waves (PP), determining the minimum PP interval over eight intervals, and exiting the fallback mode and reverting the first mode of heart stimulation when the minimum interval becomes larger than a minimum period corresponding to the selected maximum frequency for ventricular stimulation.

13. The method of claim 11 characterized in that the defined time is 30 seconds and the stable frequency is 70 beats per minute.

14. A method according to claim 9, further characterized by:
increasing the duration of the minimum atrial-ventricular delay to comply with the maximum frequency of ventricular stimulation;
selecting a post-ventricle atrial refractory period (PVARP) having a duration of the time which separates two ventricular stimulations at the maximum frequency, reduced by the value of the minimum atrial-ventricular delay; and
triggering a PVARP after stimulation of the ventricle.

15. A method according to claim 14 further characterized by providing the pacemaker with a fallback mode of operation for lowering the ventricular stimulation frequency to a stable frequency further characterized by providing a defined time, determining the occurrence of pathological P waves as a tachycardia, and operating the pacemaker in the fallback mode in response to the tachycardia occurring beyond the defined time.

16. A method according to claim 15 in which operating in the fallback mode is characterized by monitoring the interval between two consecutive P waves (PP), determining the minimum PP interval over eight intervals and exiting out of the fallback mode and reverting to the first mode of heart stimulation when the average minimum PP interval becomes larger than a minimum period corresponding to the selected maximum frequency for ventricular stimulation.

17. The method of claim 15 characterized in that the defined time is 30 seconds and the stable frequency is 70 beats per minutes.

18. A method according to claim 8 characterized in that selecting the PAARP is characterized by selecting a fraction from between 0.7 and 0.8, determining the time interval between two preceding P waves in response to the occurrence of physiological P wave, determining the average time interval of the eight preceding P waves in response to the occurrence of a pathological P wave, and multiplying the selected fraction by one of the determined time interval and the determined average.

19. Apparatus for controlling a dual-chamber pacemaker having sensors for monitoring atrial and ventricular depolarization and electrodes for atrial and ventricular pacing and a first heart stimulation mode of operation comprising:
means for monitoring P waves corresponding to atrial depolarization events;
means for initiating a selected postatrial atrial refractory period following an atrial depolarization;
means for determining that a P wave that occurs during an initiated PAARP is pathological and a P wave that occurs after an initiated PAARP is physiological; and
means for initiating a selected atrial-ventricular delay in response to a physiological P wave and for not initiating the selected atrial-ventricular delay in response to a pathological P wave.

20. The apparatus of claim 19 wherein the PAARP initiating means further comprises means for selecting the PAARP to be a fraction selected from between 0.7 and 0.8 times the time interval between two previous physiological P waves.

21. The apparatus of claim 20 wherein the fraction is 0.75.

22. The apparatus of claim 19, further comprising means for monitoring ventricular depolarization and identifying pathological ventricular depolarization, wherein the PAARP initiating means further comprises means for selecting the PAARP to be a fraction selected from between 0.7 and 0.8 times the average of the eight preceding physiological P waves in response to the occurrence of a pathological P wave or a pathological ventricular depolarization.

23. The apparatus of claim 22 wherein the fraction is 0.75.

24. The apparatus of claim 19 wherein the PAARP initiating means further comprises means for limiting the PAARP to a maximum duration between 400 and 600 ms.

25. The apparatus of claim 19, further comprising:
means for triggering an atrial escape interval having a duration equal to the PAARP in response to a P wave occurring during the PAARP; and
means for determining the longest delay as between the PAARP interval and the selected atrial escape interval triggered at the time of the previous P wave in the absence of a detection of a subsequent P wave and for controlling the pacemaker to stimulate the atrium at the end of the determined longest delay.

26. The apparatus of claim 25 further comprising means for providing the atrial-ventricular delay with a minimum duration in response to one of a detection of a P wave outside of the PAARP and an atrial stimulation.

27. The apparatus of claim 26 further comprising a comparator for comparing elapsed time since the last ventricular stimulation to a first period corresponding to a maximum frequency of stimulation; and
means for controlling the pacemaker to stimulate the ventricle at the end of the minimum atrial-ventricular delay in response to the elapsed time being greater than the first period.

28. The apparatus of claim 27 wherein the means for controlling the pacemaker to stimulate the ventricle further comprises:
means for extending the minimum atrialventricular delay to coincide with the end of the first period in response to the elapsed time being less than the first period; and
means for initiating a post-ventricle atrial refractory period (PVARP) following stimulation of the ventricle, the PVARP having a duration of the time which separates two ventricular stimulations at the maximum frequency, reduced by the value of the minimum atrial-ventricular delay.

29. The apparatus of claim 28 further comprising means for operating the pacemaker in a fallback mode of operation for lowering the ventricular stimulation frequency down to a stable frequency comprising a switch having a first state corresponding to operation in the first mode of heart stimulation in response to the pathological P waves existing for less than the defined time and a second state corresponding to operation in the fallback mode in response to the pathological P waves occurring beyond the defined time.

30. The apparatus of claim 29 further comprising means for monitoring the minimum interval between two consecutive P waves over eight cycles; and
means for placing the switch in the first state in response to the average minimum interval being larger than the first period.

31. The apparatus of claim 29 wherein the defined time is 30 seconds and the stable frequency is 70 beats per minute.

32. The apparatus of claim 29 wherein the maximum duration is 560 msec.

33. The apparatus of claim 25 wherein the PAARP initiating means further comprises means for selecting the PAARP to be a fraction selected from between 0.7 and 0.8 times one of the time interval between two preceding P waves in response to the occurrence of a physiological P wave, and the average of the interval between the eight preceding P waves in response to the occurrence of a pathological depolarization.

* * * * *

UNITED STATES PATENT AND TRADEMARK OFFICE
CERTIFICATE OF CORRECTION

PATENT NO. : 5,226,415
DATED : July 13, 1993
INVENTOR(S) : Girodo et al.

It is certified that error appears in the above—identified patent and that said Letters Patent is hereby corrected as shown below:

Column 1, line 53, "stance" should be --stance,--;

Column 5, line 61 "P" should be --P"--;

Column 6, lines 24-25 "atriumventricle" should be --atrium-ventricle--;

Column 7, line 60, after "as" insert --the model--;

Column 8, line 56, "Wenkenbach" should be --Wenkebach--;

Column 8, line 66, "mode"" should be --mode".--.

Column 10, line 23, "V"" should be --V".--.

Column 10, line 33, "Wenkenbach" should be --Wenkebach--;

Table II, line 12, "(INT v>MINPER" should be --(INT v>MINPER & INT A>MINPER)--;

Table II, line 19, the term --Z-- should appear in the functions column;

Table II, line 26, "WENC2" should not appear in the (IF) NEW STATE column;

Table II, line 27, --WENC2-- should appear in the (IF) NEW STATE column;

Table II, line 31, "ASSO" should not appear in the (IF) NEW STATE column;

UNITED STATES PATENT AND TRADEMARK OFFICE
CERTIFICATE OF CORRECTION

PATENT NO. : 5,226,415

DATED : July 13, 1993

INVENTOR(S) : Girodo et al.

It is certified that error appears in the above—identified patent and that said Letters Patent is hereby corrected as shown below:

Table II, line 32, the term --ASSO-- should appear in the (IF) NEW STATE column;

Table II, line 45, the term "C" should be deleted from the FUNCTIONS column;

Table II, footnote **, line 1, "sine" should be --since--.

Column 11, Function Key R, "ESC INT - 31 ms" should be --ESC INT + 31 ms--;

Column 11, Function Key S, "ESC INT - 125 ms" should be --ESC INT + 125 ms--;

Column 11, Function Keys L and Z, "wenckeback" should be --Wenkebach--;

Column 13, line 54, "verting" should be --verting to--;

Column 14, line 43, "postatrial" should be --post-atrial--;

Column 14, line 44, after "period" insert --(PAARP)--; and

UNITED STATES PATENT AND TRADEMARK OFFICE
CERTIFICATE OF CORRECTION

PATENT NO. : 5,226,415
DATED : July 13, 1993
INVENTOR(S) : Girodo, et al

It is certified that error appears in the above-indentified patent and that said Letters Patent is hereby corrected as shown below:

```
Column 15, line 33, "atrialventricular" should be
--atrial-ventricular--.
```

Signed and Sealed this

Third Day of May, 1994

Attest:

BRUCE LEHMAN

Attesting Officer

Commissioner of Patents and Trademarks